United States Patent
Jones

(10) Patent No.: US 9,021,863 B1
(45) Date of Patent: May 5, 2015

(54) SYSTEM FOR MEASURING BACK PRESSURE IN OPEN ENDED CHEMICAL REACTOR TUBES

(75) Inventor: Shannon Jones, La Porte, TX (US)

(73) Assignee: Turnkey Automation, Ltd., La Porte, TX (US)

( * ) Notice: Subject to any disclaimer, the term of this patent is extended or adjusted under 35 U.S.C. 154(b) by 738 days.

(21) Appl. No.: 13/158,272

(22) Filed: Jun. 10, 2011

(51) Int. Cl.
*G01N 7/00* (2006.01)
*G06F 19/00* (2011.01)

(52) U.S. Cl.
CPC ........................................ *G06F 19/70* (2013.01)

(58) Field of Classification Search
USPC ............................................................ 73/37
See application file for complete search history.

(56) References Cited

U.S. PATENT DOCUMENTS

| | | | |
|---|---|---|---|
| 6,725,706 B2 | 4/2004 | Johns et al. | |
| 6,981,422 B1* | 1/2006 | Comardo | 73/756 |
| 7,673,496 B2 | 3/2010 | Johns et al. | |
| 7,818,995 B2 | 10/2010 | Johns et al. | |
| 7,913,543 B2 | 3/2011 | Johns et al. | |

* cited by examiner

*Primary Examiner* — Paul West
(74) *Attorney, Agent, or Firm* — Buskop Law Group, PC; Wendy Buskop

(57) ABSTRACT

A system for measuring back pressure in open ended chemical reactor tubes is provided. The system can include automatic test heads or manual test head connected to a continuous real-time monitor and display device, a controller, a multiport manifold, and a plurality of umbilicals. Each umbilical can carry compressed air, sensor signals, and power to the test heads.

18 Claims, 7 Drawing Sheets

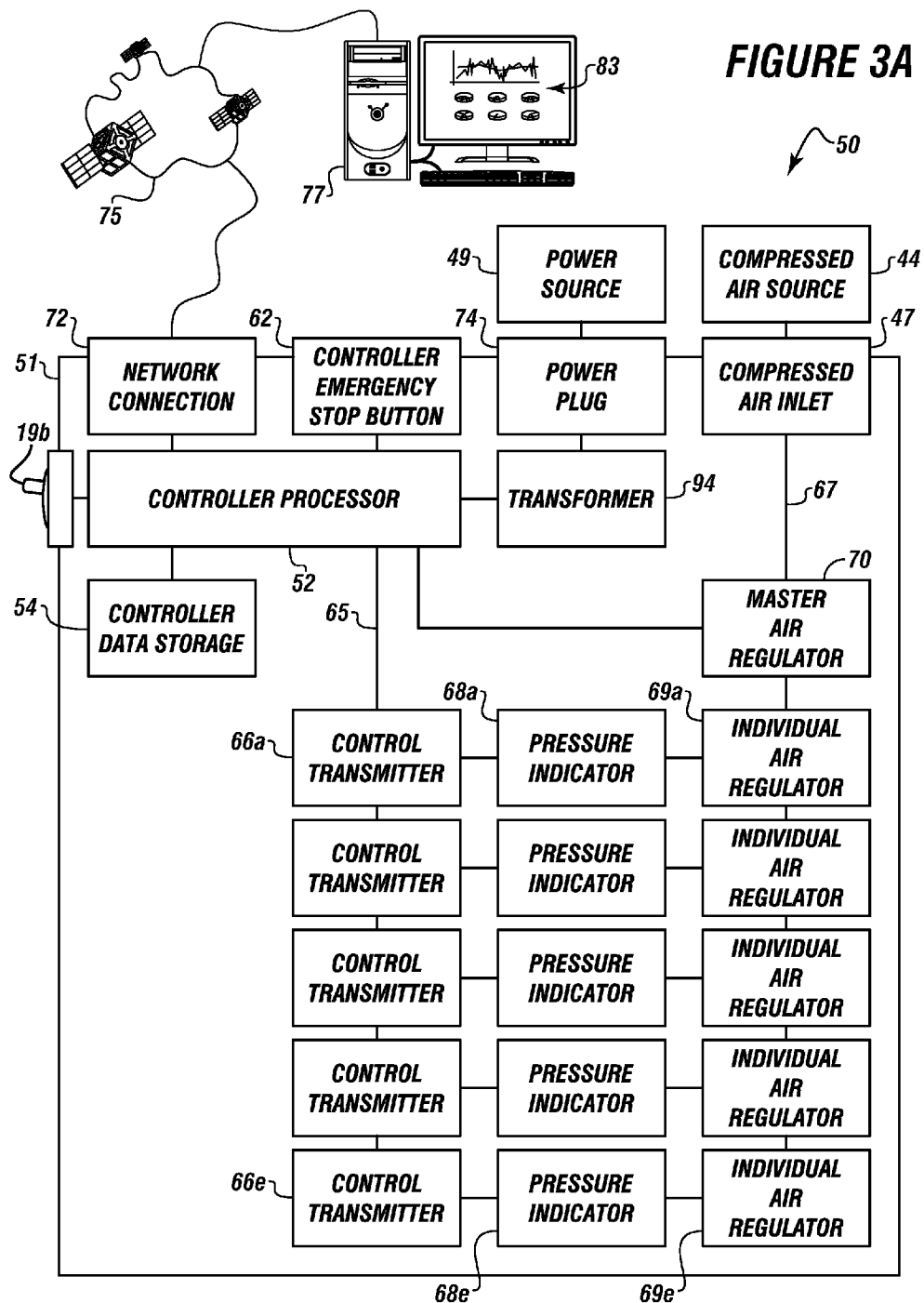

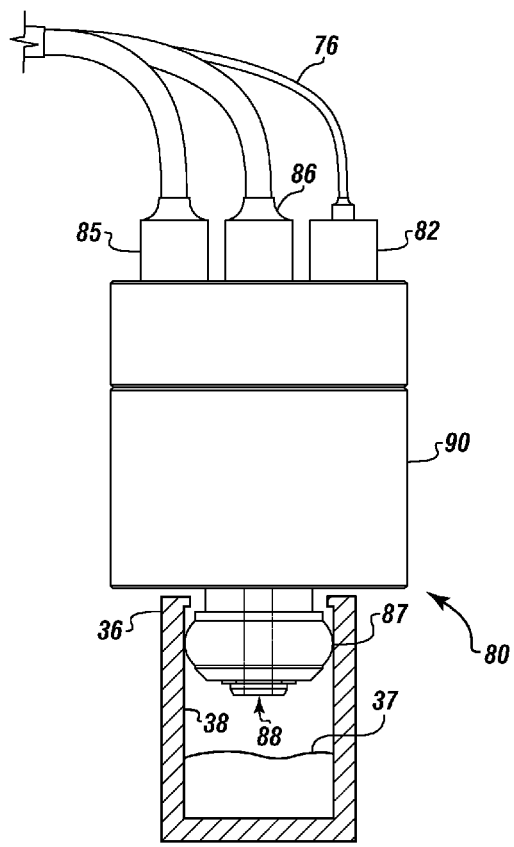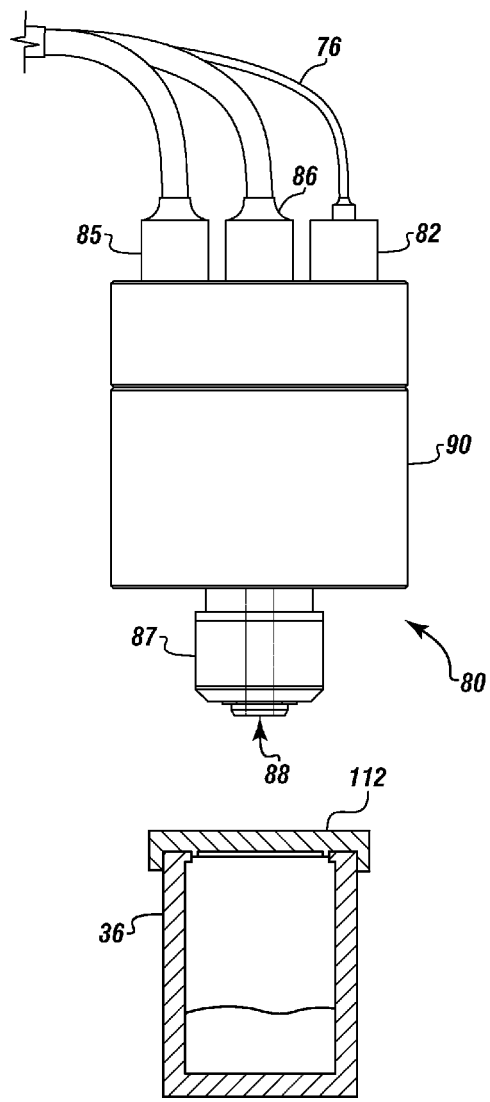

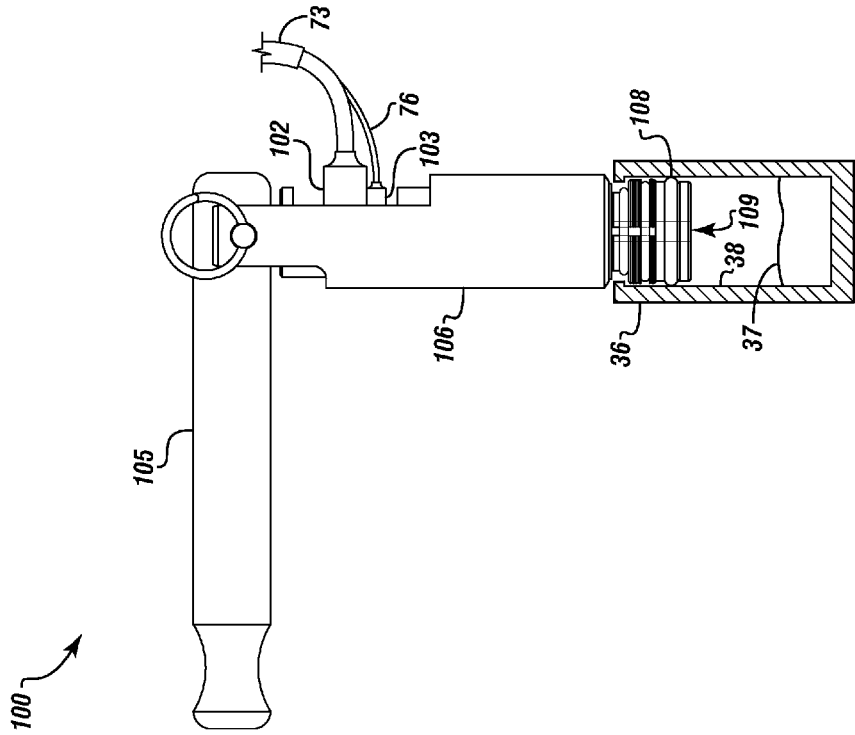
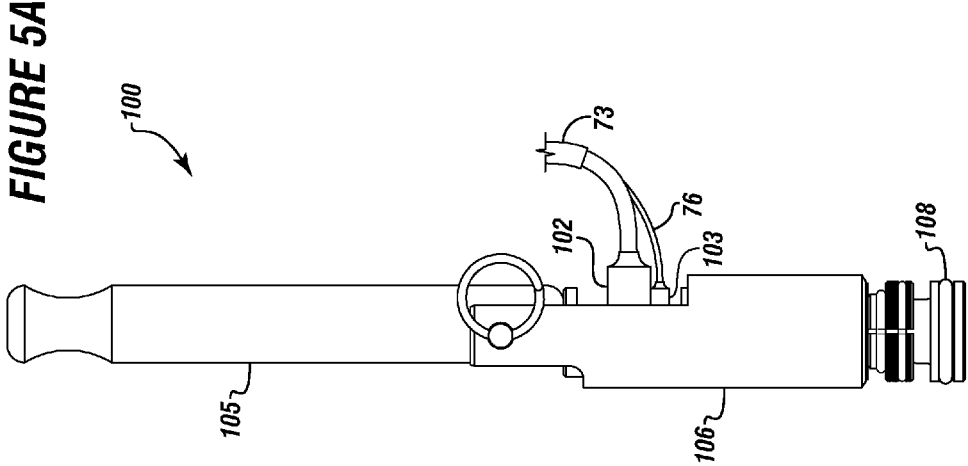

SYSTEM FOR MEASURING BACK PRESSURE IN OPEN ENDED CHEMICAL REACTOR TUBES

FIELD

The present embodiments generally relate to a system for measuring back pressure in open ended chemical reactor tubes, such as catalyst tubes for a chemical plant.

BACKGROUND

A need exists for a system for measuring back pressure in open ended chemical reactor tubes that has individually replaceable heads for the testing process.

A need exists for a system for measuring back pressure in open ended chemical reactor tubes that can accurately flow air to chemical reactor tubes individually, thereby ensuring that each chemical reactor tube is properly tested.

A need exists for system for measuring back pressure in open ended chemical reactor tubes that can continue to be used even if one of the test heads is defective or needs replacement.

The present embodiments meet these needs.

BRIEF DESCRIPTION OF THE FIGURES

The detailed description will be better understood in conjunction with the accompanying drawings as follows:

FIGS. 3A-3B depicts a detail of a controller and a controller data storage.

FIGS. 4A-4B depict detailed views of an automated test head, a chemical reactor tube, and a colored tube cap.

FIGS. 5A-5B depict detailed views of a manual test head in a pre-testing position and testing position.

The present embodiments are detailed below with reference to the listed Figures.

DETAILED DESCRIPTION OF THE EMBODIMENTS

Before explaining the present system in detail, it is to be understood that the system is not limited to the particular embodiments and that it can be practiced or carried out in various ways.

The present embodiments relate to a system for measuring back pressure in open ended chemical reactor tubes.

The system can include: a continuous real-time monitor and display connected to a programmable controller, a manifold connected to the continuous real-time monitor and display, a plurality of individual umbilicals connected to the manifold, and at least one of the plurality of test heads is connected to at least one of the plurality of individual umbilicals. Each test head can be automatic or manual.

The automated test heads can be remotely controlled, allowing for a fewer number of employees to be present near high pressure catalysts; thereby improving safety for the employees. For example, the high pressure catalysts, which can be an explosive powder, can be located in a confined space where it can be dangerous for employees to be present.

The system can function faster than manual processes currently available because the pressure heads can enable quicker seals without requiring a person to hold the seals in place; thereby preventing leakage.

The system can be versatile, because the system can include test heads of different sizes configured to accommodate different sized chemically loaded tubes, chemically unloaded tubes, partially filled chemical tubes, partially filled with catalyst tubes, or the like.

Test heads of the system can be individually replaceable, providing a system with a longer life span. Also, the continuous real-time monitor and display device can be individually replaced without replacing the entire system.

The system can have a lower maintenance cost than current devices, in-part because if one umbilical of the system becomes defective, that umbilical can be replaced without replacing the entire system.

Figure 1A:
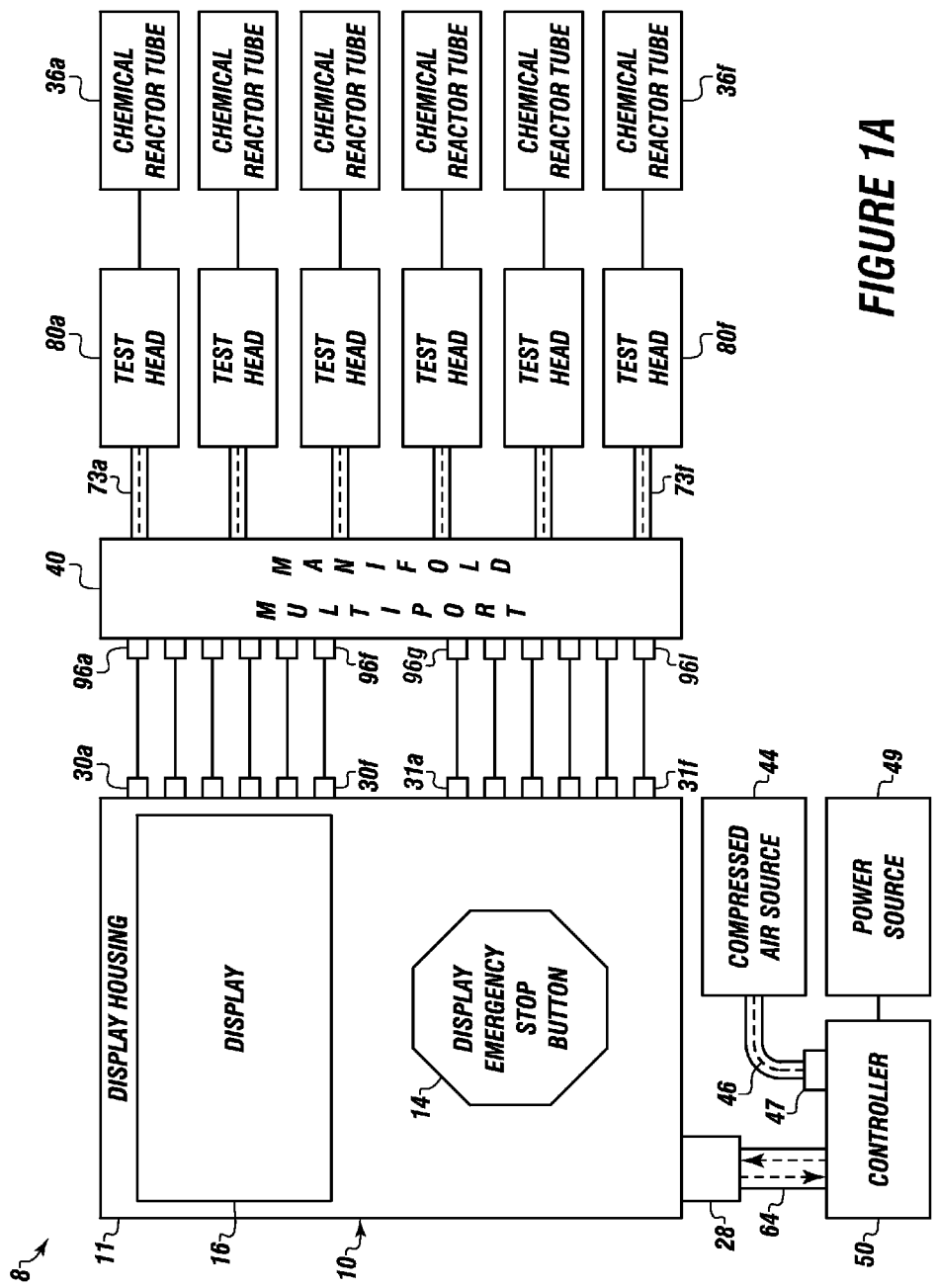
FIG. 1A depicts an overview of the system.

Turning now to the Figures, FIG. 1A depicts an overview of the system 8. The system 8 can include a continuous real-time monitor and display device 10.

The continuous real-time monitor and display device 10 can be bi-directionally connected to a controller 50, such as through a bi-directional multiline air, power, and signal line 64.

The controller 50 can bi-directionally communicate compressed air, power, and sensor signals to and from the continuous real-time monitor and display device 10. The bi-directional multiline air, power, and signal line 64 can communicate into the continuous real-time monitor and display device 10 through a bi-directional multiline air, power, and signal port 28.

The controller 50 can be in communication with a power source 49 for receiving power therefrom. The controller 50 can also be in communication with a compressed air source 44 through a compressed air inlet 47 for receiving compressed air 46 therefrom.

The continuous real-time monitor and display device 10 can have a display housing 11.

The continuous real-time monitor and display device 10 can have a display emergency stop button 14 located on the display housing 11. In one or more embodiments, the display emergency stop button 14 can be in communication with an air regulator and a processor with computer instructions that allow a local operator to stop the operation of the system 8.

The continuous real-time monitor and display device 10 can have a display 16. Embodiments of the continuous real-time monitor and display device 10 can have a switch that can be used to turn the system 8 on and off. The switch can be mounted to the controller 50 or the display housing 11, and can be in communication with a controller processor.

The system 8 can have a multiport manifold 40 in communication with the continuous real-time monitor and display device 10. For example, the continuous real-time monitor and display device 10 can have a plurality of first compressed air outlets, such as first compressed air outlets 30a and 30f, in communication with a plurality of manifold inlets, such as manifold inlets 96a and 96f, to communicate into the multiport manifold 40.

The plurality of first compressed air outlets 30a and 30f and the plurality of manifold inlets 96a and 96f can be quick disconnects, which can allow for fast assembly of the system 8, such as a set-up time of less than 10 minutes.

The plurality of first compressed air outlets 30a and 30f can be configured to flow the compressed air 46 from the display housing 11 to each test head seal portion of a plurality of test heads, such as test heads 80a and 80f. The compressed air 46 can expand each test head seal portion against an inner wall of one of a plurality of chemical reactor tubes, such as chemical reactor tubes 36a and 36f.

The continuous real-time monitor and display device 10 can have a plurality of second compressed air outlets, such as second compressed air outlets 31a and 31f, in communication with the multiport manifold 40 for flowing compressed air 46 from the display housing 11 through each of the plurality of the test heads 80a and 80f and into each of the chemical reactor tubes 36a and 36f.

The plurality of second compressed air outlets 31a and 31f can be in communication with the multiport manifold 40 through a plurality of manifold inlets, such as manifold inlets 96g and 96l, which can also be quick disconnects.

The multiport manifold 40 can be in communication with the plurality of test heads 80a and 80f, through a plurality of individually removable and replaceable test head umbilicals, such as individually removable and replaceable test head umbilicals 73a and 73f.

In operation, the multiport manifold 40 can transmit compressed air 46 to the continuous real-time monitor and display device 10. The compressed air 46 transmitted from the multiport manifold 40 to the continuous real-time monitor and display device 10 can be individually regulated and controlled within each of the plurality of individually removable and replaceable test head umbilicals 73a and 73f. In one or more embodiments, each of the plurality of individually removable and replaceable test head umbilicals 73a and 73f can have a different pressure.

The plurality of test heads 80a and 80f can be in communication with the plurality of chemical reactor tubes 36a and 36f. The plurality of individually removable and replaceable test head umbilicals 73a and 73f can include groups of similar pressurized air lines, such that a first portion of the plurality of test heads 80a and 80f can measure loaded chemical reactor tubes 36a and 36f at a first pressure, a second portion of the plurality of test heads 80a and 80f can measure partially loaded chemical reactor tubes 36a and 36f at a second pressure, and a third portion of the plurality of test heads 80a and 80f can measure empty chemical reactor tubes 36a and 36f at a third pressure. As such, the system 8 can provide for faster group analysis of various chemical reactor tubes 36a and 36f at various pressures.

In operation, compressed air 46 can be transmitted through the plurality of test heads 80a and 80f to simultaneously measure pressure in the chemical reactor tubes 36a and 36f and transmit the measured pressure as sensor signals to the controller 50.

The system 8 can be modular, which makes the system 8 easy to repair. The system 8 can also be easy to maintain, in-part because each component of the system can be individually cleaned without having to shut down and disassemble the entire system 8. For example, one test head of the plurality of test heads 80a and 80f can be removed and cleaned while the remainder of the system 8 continuous to operate; providing a major safety improvement over current test systems.

Figure 1B:
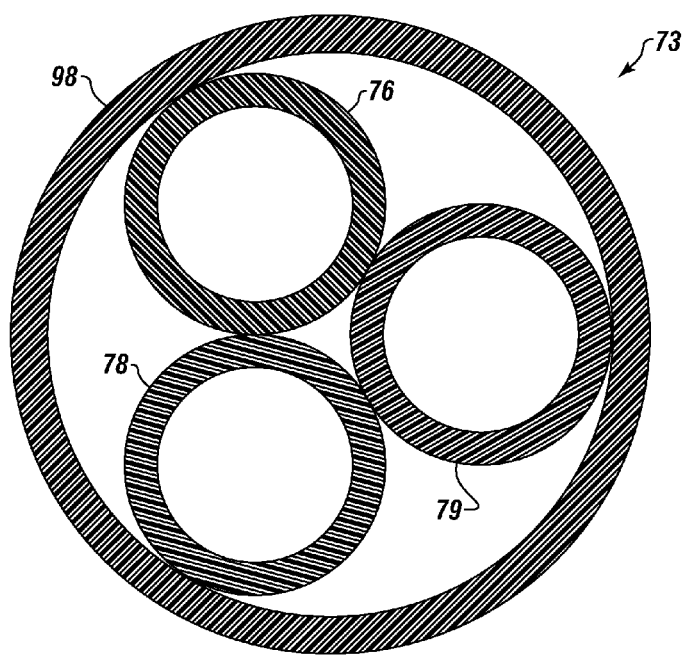
FIG. 1B depicts a cross section of an individually removable and replaceable test head umbilical.

FIG. 1B depicts a cross section of an individually removable and replaceable test head umbilical 73.

The individually removable and replaceable test head umbilical 73 can include a signal line 76, an air line 78, and a power line 79, which can all be disposed within a polymer tape 98.

The signal line 76, air line 78, and power line 79 can extend parallel to each other within the polymer tape 98.

Figure 2:
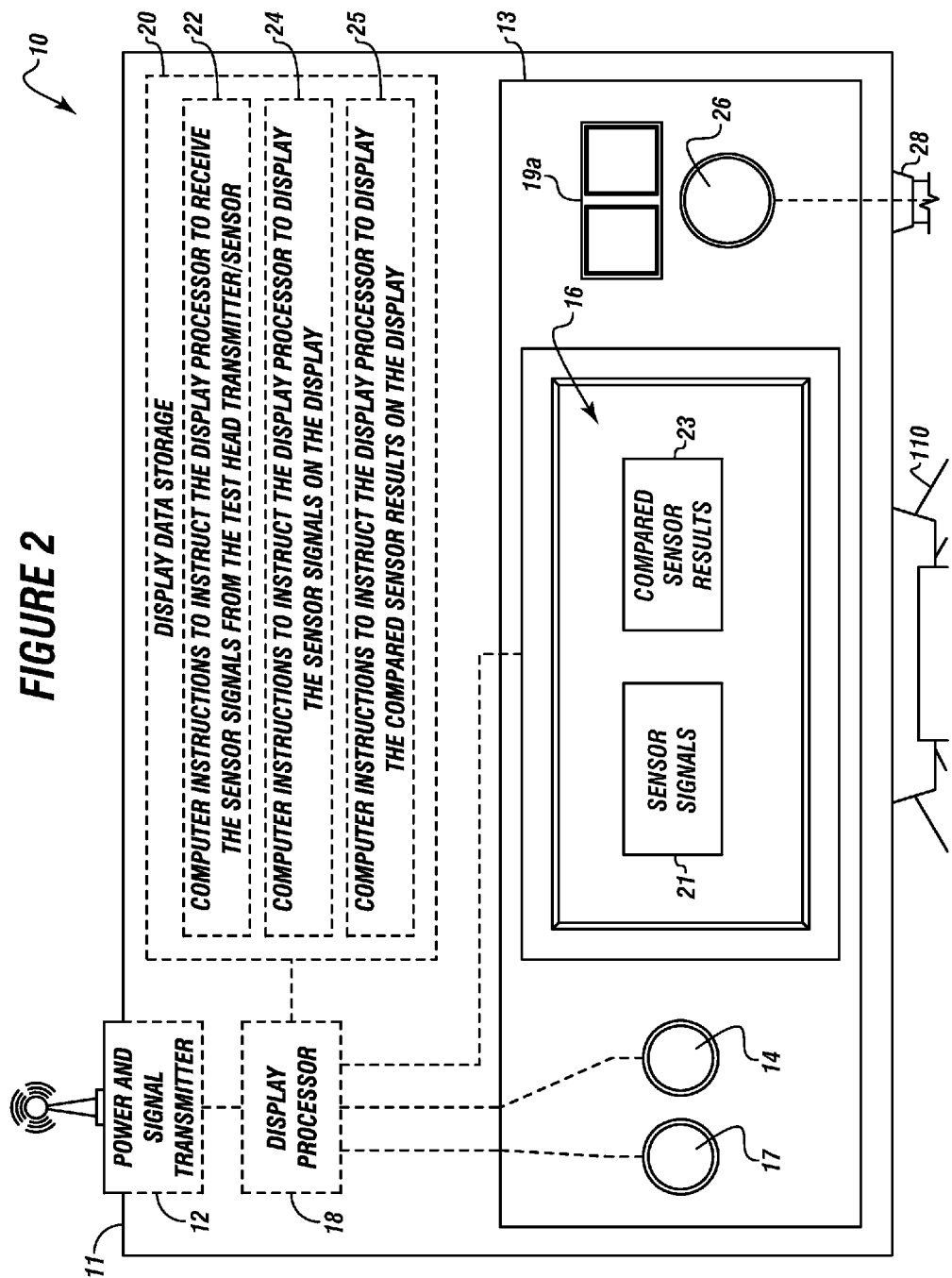
FIG. 2 depicts a detailed view of a continuous real-time monitor and display device.

FIG. 2 depicts a detailed view of an embodiment of the continuous real-time monitor and display device 10. The continuous real-time monitor and display device 10 can provide for real-time display of sensor signals 21 and compared sensor results 23. For example, the continuous real-time monitor and display device 10 can continually update the display 16 from about every 1 second to about every 5 seconds to present the sensor signals 21 and compared sensor results 23 from each test head.

The continuous real-time monitor and display 10 can include the display housing 11 with a face plate 13. The display housing 11 and face plate 13 can be an aluminum box housing with a door, which can be sealed to enable an airtight and watertight connection between the aluminum box and the door.

The continuous real-time monitor and display 10 can be supported on a tripod 110. The tripod 110 can be a collapsible foldable support structure.

The display housing 11 can include a power and signal transmitter 12, such as a mini-transmitter model A-10 available from WIKA Instrument Corporation. The power and signal transmitter 12 can be from about 1 inch long to about 3 inches long.

The power and signal transmitter 12 can be in communication with a display processor 18 in the display housing 11. The display processor 18 can be in communication with a display data storage 20 in the display housing 11.

The display data storage 20 can have computer instructions to instruct the display processor to receive the sensor signals from the test head transmitter/sensor 22.

The display data storage 20 can have computer instructions to instruct the display processor to display the sensor signals on the display 24.

The display data storage 20 can have computer instructions to instruct the display processor to display the compared sensor results on the display 25.

In operation, the sensor signals 21 can be compared to customer preset pressure limits to form the compared sensor results 23. The continuous real-time monitor and display device 10 can be configured to present the sensor signals 21 from the test head transmitter/sensors and the compared sensor results 23 from the controller in real-time.

The face plate 13 can have a touch start button 17. The touch start button 17 can be a mechanical button mounted to the face plate 13. The touch start button 17 can be in communication with the display processor 18.

The face plate 13 can include the display emergency stop button 14, which can be in communication with the controller and the display processor 18, and can be pressed to actuate a stop of the flow of compressed air and sensor signals to and from the test heads. The display emergency stop button 14 can be used to quickly shut down chemical reactor tubes that might be over pressuring, providing an important safety benefit.

The display 16 can be disposed on the face plate 13 and can be electronic. The display 16 can be a graphical user interface configured to graphically present the sensor signals 21 and compared sensor results 23 to users. The display 16 can be in communication with the display processor 18.

The face plate 13 can include a test push button 26 in communication with the bi-directional multiline air, power, and signal port 28 on the display housing 11. The bi-directional multiline air, power, and signal port 28 can receive the sensor signals 21 from the controller. The test push button 26 can be used to start a particular compressed air test.

The face plate 13 can have an on/off switch 19a for turning the system on and off.

In operation, compressed air 46 can be transmitted through the plurality of test heads to simultaneously measure pressure in the chemical reactor tubes and transmit the measured pressure as the sensor signals 21 to the controller. The controller can use the sensor signals 21 along with data stored in a controller data storage to compute a comparison between the sensed pressure and customer preset pressure values, forming the compared sensor results 23.

FIG. 3A depicts a detail of the controller 50 with a controller housing 51.

The controller 50 can be in communication with the power source 49 through a power plug 74. The controller 50 can have a transformer 94 in communication with the power plug 74 for transforming A/C current to D/C current for operating gauges, transmitters, processors, transmitter/sensors and other components of the system.

The power plug 74 can be a 110 volt plug configured to receive power to operate a controller processor 52 and to power the controller 50. The power plug 74 can also be used to power the continuous real-time monitor and display device, and to flow power through each individually removable and replaceable test head umbilical to power each of the plurality of test head.

The controller 50 can be in communication with the compressed air source 44 through the compressed air inlet 47 for supplying the compressed air to the controller 50 and other portions of the system including the continuous real-time monitor and display device, the multiport manifold, and the plurality of test heads.

The controller processor 52 can be in communication with the transformer 94, a controller data storage 54, a network connection 72, the continuous real-time monitor and display device, and the compressed air source 44, such as through a controller emergency stop button 62.

The network connection 72 can be an Ethernet port for connecting the controller 50 and the controller processor 52 to a network 75, such as the internet, allowing for remote operation of the system by a user. For example, the controller 50 can present an executive dashboard 83 on a client device 77 using the network 75.

The controller emergency stop button 62 can be used to ensure that a local operator or user can quickly stop the flow of compressed air to the chemical reactor tubes, such as if pressure in the chemical reactor tubes is at a dangerous level.

The controller 50 can include a plurality of control transmitters, such as control transmitter 66a and 66e, which can be small or mini transmitters. Each of the plurality of control transmitters 66a and 66e can be in communication with the controller processor 52 through a controller signal line 65.

The controller 50 can include a plurality of pressure indicators, such as pressure indicators 68a and 68e. Each of the plurality of pressure indicators 68a and 68e can be in communication with one of a plurality of individual air regulators, such as individual air regulators 69a and 69e.

The plurality of pressure indicators 68a and 68e, which can be pressure gauges, can communication with the controller processor 52 through the plurality of control transmitters 66a and 66e and the controller signal line 65. Each of the plurality of pressure indicators 68a and 68e can be in communication with a test head transmitter/sensor and one of a plurality of individual air regulators 69a and 69e.

The controller 50 can include a master air regulator 70 connected to the plurality of individual air regulators 69a and 69e. The master air regulator 70 can be in communication with the controller emergency stop button 62 through the controller processor 52 through a controller air line 67. The controller can have an on/off switch 19b for turning the controller on and off.

Figure 3B:
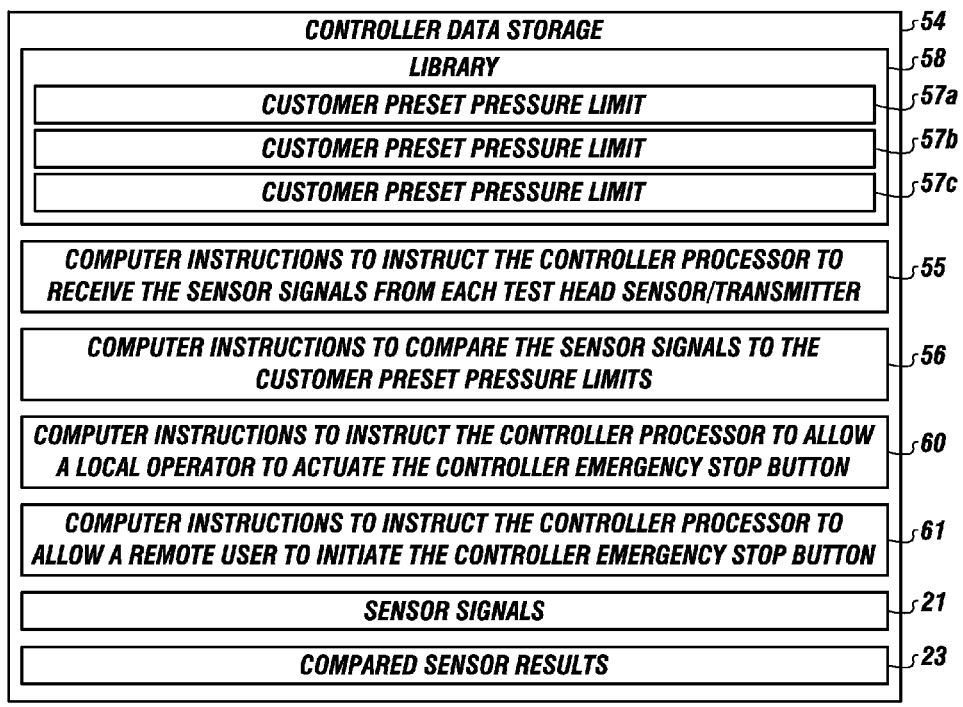

FIG. 3B depicts a detail of the controller data storage 54.

The controller data storage 54 can have various computer instructions programmed therein. For example, the controller data storage 54 can have a library 58 including customer preset pressure limits 57a, 57b, and 57c.

The controller data storage 54 can have computer instructions to instruct the controller processor to receive the sensor signals from each test head sensor/transmitter 55.

The controller data storage 54 can have computer instructions to compare the sensor signals to the customer preset pressure limits 56.

The controller data storage 54 can have computer instructions to instruct the controller processor to allow a local operator to actuate the controller emergency stop button 60.

The controller data storage 54 can have computer instructions to instruct the controller processor to allow a remote user to initiate the controller emergency stop button 61.

The sensor signals 21 and the compared sensor results 23 can be stored in the controller data storage 54.

In operation, the controller can use the sensor signals 21, data stored in the controller data storage 54, the library 58 of customer preset pressure limits 57a, 57b and 57c, and the various computer instructions in the controller data storage 54, including comparison algorithms, in order to compute a comparison between the sensed pressures of the sensor signals and the customer preset pressure limits 57a, 57b and 57c; thereby forming the compared sensor results 23.

The controller can use the controller processor and other equipment to transmit the compared sensor results 23 and/or the sensor signals 21 to the display of the continuous real-time monitor and display device.

FIGS. 4A-4B depict an automated test head 80, which can be air actuated. The automatic test head 80 can have a test head body 90, which can be a bi-directional multiline compress test head body.

The automated test head 80 can have a first test head compressed air inlet port 85 and a second test head compressed air inlet port 86.

In operation, the first test head compressed air inlet port 85 can flow compressed air into the test head body 90 to expand and seal a test head seal portion 87 against the inner wall 38 of a chemical reactor tube 36.

FIG. 4A shows the test head seal portion 87 sealed against the inner wall 38 of the chemical reactor tube 36, and FIG. 4B shows the automated test head 80 removed from the chemical reactor tube 36.

Simultaneously, while using the compressed air to seal the automated test head 80 to the chemical reactor tube 36, compressed air can be transmitted into the automated test head 80 through the second test head compressed air inlet port 86.

The second test head compressed air inlet port 86 can flow compressed air through the test head body 90 and out of a test head seal outlet 88 into the chemical reactor tube 36; thereby enabling the test head transmitter/sensor 82 to measure the pressure in the chemical reactor tube 36. In operation, the system can be used to measure the pressure in loaded, partially loaded, and unloaded chemical reactor tubes 36 for comparison purposes.

The automated test head 80 can be used to simultaneously measure pressure in the chemical reactor tube 36 and transmit the measured pressure as sensor signals to the controller through a signal line 76, which can also be called a transmitter connection.

The first test head compressed air inlet port 85, the second test head compressed air inlet port 86, and the signal line 76 can each be a portion of one of the plurality of individually removable and replaceable test head umbilicals.

The test head transmitter/sensor 82 can be connected to the automated test head 80 and the signal line 76, which can transmit the sensor signals from the automated test head 80 to the controller processor of the controller.

The automated test head 80 can be engaged within the chemical reactor tube 36, as shown in FIG. 4A. The chemical reactor tube 36 can be loaded with a catalyst 37.

To use the automated test head 80, an operator can first connect the individually removable and replaceable test head umbilical to the miniport manifold.

The operator can then connect the multiport manifold to the continuous real-time monitor and display device.

The operator can then connect the continuous real-time monitor and display device to the controller.

The operator can power the controller, such as by providing electricity to the controller, which can in-turn power the entire system.

The operator can then allow compressed air from the compressed air source to enter the controller, which can pressurize the entire system. The pressure of the compressed air can vary depending on the chemical reactor tube 36 being analyzed. For example, the pressure of the compressed air can range from about 0 pounds per square inch to about 1000 pounds per square inch, such as 90 pounds per square inch, depending upon the application.

The customer preset pressure limits can be inputted into the controller data storage.

The automated test head 80 can be tested to ensure that the compressed air is flowing, and to ensure that the test head transmitter/sensor 82 is operational using a test stand of the chemical reactor tube 36 with a known pressure. The entire system can be properly calibrated to within +/−1 percent.

Next, the automated test head 80 can be inserted into the chemical reactor tube 36, such as at a customer site.

The operator can initiate pressurization of the automated test head 80 in the chemical reactor tube 36 by activating the touch start button of the display in the continuous real-time monitor and display device.

The controller can receive the sensor signals from each of the test head transmitter/sensor 82. The controller can then compare the sensor signals to the customer preset limits.

The controller can transmit the compared sensor results to the display every two seconds to present the compared sensor results. The compared sensor results can also be transmitted to a network, such as a satellite network or the internet to client devices; enabling remote users to monitor the process, such as with an executive dashboard on the client device.

The compared sensor results and the sensor signals can be stored in the controller data storage. The operator can print out any data in the controller data storage by connecting the network connection of the controller to a printer.

A colored tube cap 112 can be placed over the chemical reactor tube 36 after testing is complete.

FIGS. 5A-5B depict a detailed view of an embodiment of a manual test head 100. FIG. 5A shows the manual test head 100 with a handle 105 extending parallel to a manual test head body 106, and FIG. 5B shows the manual test head 100 with the handle 105 extending perpendicular to the manual test head body 106. The manual test head body 106 can be pivotably connected to the handle 105.

The manual test head 100 can be operated in a similar manner as the automated test head of FIGS. 4A-4B, however, the manual test head 100 can have the handle 105 for connecting to an individually removable and replaceable test head umbilicals 73.

A manual test head seal portion 108 can be connected to the manual test head body 106.

A manual test head seal outlet 109 can be centrally formed in the manual test head seal portion 108.

A manual test head compressed air inlet port 102, which can be a portion of the individually removable and replaceable test head umbilicals 73, can flow compressed air through the manual test head body 106 and out of the manual test head seal outlet 109 to a chemical reactor tube 36.

A manual test head transmitter/sensor 103 can be connected to the manual test head body 106 for sensing pressure in the chemical reactor tube 36, and transmitting the sensed pressure as a sensor signal through a signal line 76, which can be in communication with the controller processor of the controller.

The manual test head 100 can be placed into the chemical reactor tube 36 using the handle 105, which can be axially aligned with the manual test head body 106.

To operate the manual test head 100, the handle 105 can be pivoted to be oriented at a angle ranging from 90 degrees to 180 degrees to the manual test body 106 as shown in FIG. 5B; thereby causing the manual test head seal portion 108 to extend and form a seal with the inner wall 38 of the chemical reactor tube 36 and allowing the compressed air to pass into the chemical reactor tube 36 through the manual test head seal outlet 109. In this Figure, the chemical reactor tube 36 is shown loaded with catalyst 37.

The manual test head transmitter/sensor 103 can then sense pressure in the chemical reactor tube 36 and transmit the sensed pressure as sensor signals to the controller processor of the controller.

While these embodiments have been described with emphasis on the embodiments, it should be understood that within the scope of the appended claims, the embodiments might be practiced other than as specifically described herein.

What is claimed is:

1. A system for measuring back pressure in chemical reactor tubes, the system comprising:
   a. a continuous real-time monitor and display device comprising:
      (i) a display housing;
      (ii) a power and signal transmitter in the display housing;
      (iii) a display emergency stop button connected to the power and signal transmitter;
      (iv) a display mounted to the display housing and configured to present sensor signals and compared sensor results;
      (v) a display processor connected to the display and to a plurality of test head transmitter/sensors, wherein the display processor is configured to receive the sensor signals from the plurality of test head transmitter/sensors;
      (vi) a display data storage connected to the display processor, wherein the display data storage comprises:
         1. computer instructions to instruct the display processor to receive the sensor signals from the test head transmitter/sensors;
         2. computer instructions to instruct the display processor to display the sensor signals on the display; and
         3. computer instructions to instruct the display processor to display the compared sensor results on the display;
      (vii) a test push button mounted in the display housing and configured to initiate flow of compressed air from the display housing;
      (viii) a bi-directional multiline air, power, and signal port formed in the display housing and configured to conjunctively receive and transmit: the compressed air, power, and the sensor signals from the continuous real-time monitor and display device;

(ix) a plurality of first compressed air outlets formed in the display housing and configured to flow the compressed air from the display housing to each test head seal portion of a plurality of test heads, wherein the compressed air expands each test head seal portion against an inner wall of a chemical reactor tube to each chemical reactor tube; and (x) a plurality of second compressed air outlets formed in the display housing and configured to flow the compressed air from the display housing through each of the plurality of the test heads and into each sealed chemical reactor tube;

b. a multiport manifold connected to the continuous real-time monitor and display device via the plurality of first compressed air outlets and the plurality of second compressed air outlets, wherein the multiport manifold is configured to transmit the compressed air to each of a plurality of individually removable and replaceable test head umbilicals connected between the multiport manifold and the plurality of test heads, wherein at least one of the plurality of test heads is connected to at least one of the plurality of individually removable and replaceable test head umbilicals, and wherein each test head comprises:

(i) a test head body connected to one of the individually removable and replaceable test head umbilicals, wherein the test head body supports the test head seal portion, and wherein the test head body comprises:

1. a first test head compressed air inlet port engaged with one of the individually removable and replaceable test head umbilicals and configured to receive and flow the compressed air into the test head body to cause the test head seal portion to expand and form one of the sealed chemical reactor tubes;

2. a second test head compressed air inlet port configured engage with one of the individually removable and replaceable test head umbilicals and to receive and flow the compressed air into the test head body and out through a test head seal outlet into one of the sealed chemical reactor tubes; and 3. a signal line in the test head body, wherein the test head sensor/transmitter is engaged with the signal line and connected to one of the individually removable and replaceable test head umbilicals, and wherein each test head sensor/transmitter is configured to sense pressure in one of the sealed chemical reactor tubes;

c. a bi-directional multiline air, power, and sensor signal line connected to the continuous real-time monitor and display device;

d. a controller connected to the bi-directional multiline air, power, and signal line configured to flow the compressed air, power, and sensor signals bi-directionally between the controller and the continuous real-time monitor and display device, wherein the controller comprises:

(i) a controller housing;
(ii) a compressed air inlet in the controller housing configured to receive the compressed air from a compressed air source;
(iii) a controller processor in the controller housing;
(iv) a controller data storage connected to the controller processor comprising:
1. a controller emergency stop button mounted to the controller housing and connected to the controller processor;
2. a library of customer preset pressure limits;
3. computer instructions to instruct the controller processor to receive the sensor signals from each test head sensor/transmitter;
4. computer instructions to instruct the controller processor to compare the sensor signals to the customer preset pressure limits, wherein:
   a. the compressed air is blown into the sealed chemical reactor tubes;
   b. the sensor signals are transmitted to the controller from the test head sensor/transmitters;
   c. the controller compares the sensor signals to the customer preset pressure limits; and
   d. the controller transmits the compared sensor results to the display while the display presents the sensor signals;
5. computer instructions to instruct the controller processor to allow a local operator to actuate an emergency stop of the controller; and
6. computer instructions to instruct the controller processor to allow a remote user to initiate the emergency stop of the controller;

(v) a plurality of controller transmitters connected to the controller processor, wherein the plurality of controller transmitters are configured to: receive the sensor signals from the test head transmitter/sensors;
(vi) a plurality of pressure indicators mounted on the controller housing, wherein each pressure indicator is in communication with one of the plurality of controller transmitters;
(vii) a plurality of individual air regulators, wherein each individual air regulator is connected to one of the plurality of pressure indicators, and wherein each individual air regulator is configured to individually increase or decrease a flow of the compressed air to one of the plurality of test heads;
(viii) a master air regulator connected between the controller emergency stop button and the plurality of individual air regulators;
(ix) a network connection mounted to the controller housing and in communication with the controller processor and a network; and
(x) a power plug connected to the controller processor and configured to receive power from a power source.

2. The system of claim 1, further comprising a colored tube cap configured to be disposed on each chemical reactor tube after testing of the chemical reactor tube, and to identify each chemical reactor tube, enabling an operator to easily identify the chemical reactor tubes for replacement.

3. The system of claim 1, further comprising a transformer disposed in the controller between the power source and the controller processor.

4. The system of claim 1, wherein the multiport manifold and the controller have a plurality of quick disconnects for engagement with air supply conduits.

5. The system of claim 1, wherein the individually removable and replaceable test head umbilicals have a power line, the signal line, and an air line wrapped with a polymer tape.

6. The system of claim 1, wherein the power source is a 24 volt DC continuous supply power source.

7. The system of claim 1, further comprising a tripod for supporting the continuous-real time monitor and display device.

8. The system of claim 1, wherein the plurality of pressure indicators includes from two pressure indicators to six pressure indicators, and wherein the plurality of individual air regulators includes from two air regulators to six air regulators.

9. The system of claim 1, wherein the multiport manifold comprises from twelve compressed air conduits to sixty compressed air conduits.

10. A system for measuring back pressure in chemical reactor tubes with manual test heads, the system comprising:
  a. a continuous real-time monitor and display device comprising:
    (i) a display housing;
    (ii) a power and signal transmitter in the display housing;
    (iii) a display emergency stop button connected to the power and signal transmitter;
    (iv) a display mounted to the display housing configured to present sensor signals and compared sensor results;
    (v) a display processor connected to the display and to a manual test head transmitter/sensor, wherein the display processor is configured to receive the sensor signals from the manual test head transmitter/sensor;
    (vi) a display data storage connected to the display processor, wherein the display data storage comprises:
      1. computer instructions to instruct the display processor to receive the sensor signals from the manual test head transmitter/sensor;
      2. computer instructions to instruct the display processor to display the sensor signals on the display; and
      3. computer instructions to instruct the display processor to display the compared sensor signals on the display;
    (vii) a test push button mounted in the display housing and configured to initiate flow of compressed air from the display housing;
    (viii) a bi-directional multiline air, power, and signal port formed in the display housing and configured to conjunctively receive and transmit: the compressed air, power, and signals from the continuous real-time monitor and display device;
    (ix) a plurality of first compressed air outlets formed in the display housing and configured to flow the compressed air from the display housing to each manual test head seal portion of a plurality of manual test heads, wherein the compressed air expands each manual test head seal portion against an inner wall of a chemical reactor tube, forming a sealed chemical reactor tube; and
    (x) a plurality of second compressed air outlets formed in the display housing and configured to flow the compressed air from the display housing through each of the plurality of the manual test heads and into each sealed chemical reactor tube;
  b. a multiport manifold connected to the continuous real-time monitor and display device via the plurality of first compressed air outlets and the plurality of second compressed air outlets, wherein the multiport manifold is configured to transmit the compressed air to each of a plurality of individually removable and replaceable test head umbilicals connected between the multiport manifold and each of the plurality of manual test heads, wherein each manual test head is connected to one of the plurality of individually removable and replaceable test head umbilicals, and wherein each manual test head comprises:
    (i) a handle connected to one of the individually removable and replaceable test head umbilicals;
    (ii) a manual test head body pivotably connected to the handle, wherein the manual test head body supports the manual test head seal portion when the handle is disposed at an angle from the manual test head body ranging from ninety degrees to one hundred eighty degrees, and wherein the manual test head seal portion seals the chemical reactor tube forming the sealed chemical reactor tube, and wherein the manual test head body comprises:
      1. a manual test head compressed air inlet port configured to flow the compressed air into the manual test head body;
      2. a manual test head seal outlet configured to flow the compressed air from the manual test head body to the sealed chemical reactor tube; and
      3. the manual test head transmitter/sensor connected to the manual test head body configured to sense pressure in the sealed chemical reactor tube and transmit the sensor signals to a control processor;
  c. a bi-directional multiline air, power, and signal line connected to the continuous real-time monitor and display device;
  d. a controller connected to the bi-directional multiline air, power, and signal line configured to flow the compressed air, power, and signals bi-directionally between the controller and the continuous real-time monitor and display device, wherein the controller comprises:
    (i) a controller housing;
    (ii) a compressed air inlet in the controller housing configured to receive the compressed air from a compressed air source;
    (iii) the controller processor in the controller housing;
    (iv) a controller data storage connected to the controller processor comprising:
      1. a library of customer preset pressure limits;
      2. computer instructions to instruct the controller processor to compare the sensor signals from each of the manual test head transmitter/sensor to the customer preset pressure limits, wherein the manual test head transmitter/sensor is configured to sense pressure in the sealed chemical reactor tube and transmit the sensed pressure to the controller processor as the sensor signals, and wherein:
        a. the compressed air is blown into the sealed chemical reactor tube;
        b. the sensor signals are transmitted to the controller from the manual test head transmitter/sensor;
        c. the controller compares the sensor signals to the customer preset pressure limits; and
        d. the controller transmits the compared sensor signals to the display while the display presents the sensor signals;
      3. computer instructions to instruct the controller processor to allow a local operator to actuate an emergency stop; and
      4. computer instructions to instruct the controller processor to allow a remote user to initiate the emergency stop;
    (v) a controller emergency stop button mounted to the controller housing and connected to the controller processor;
    (vi) a plurality of controller transmitters connected to the controller processor, wherein the plurality of controller transmitters are configured to: receive the sensor signals from the manual test head transmitter/sensor and transmit system information to the manual test head transmitter/sensor;
    (vii) a plurality of pressure indicators mounted on the controller housing, wherein each pressure indicator is in communication with one of the plurality of controller transmitters;

(viii) a plurality of individual air regulators, wherein each individual air regulator is connected to one of the plurality of pressure indicators, and wherein each individual air regulator is configured to individually increase or decrease a flow of the compressed air to the manual test head transmitter/sensor;

(ix) a master air regulator connected between the controller emergency stop button and each of the plurality of individual air regulators;

(x) a network connection mounted to the controller housing and in communication with the controller processor and a network; and (xi) a power plug connected to the controller processor and configured to receive power from a power source.

11. The system of claim 10, further comprising a colored tube cap configured to be disposed on each chemical reactor tube after testing of the chemical reactor tube and to identify each chemical reactor tube, enabling an operator to easily identify the chemical reactor tubes for replacement.

12. The system of claim 10, further comprising a transformer disposed in the controller between the power source and the controller processor.

13. The system of claim 10, wherein the multiport manifold and the controller each have a plurality of quick disconnects for engagement with air supply conduits.

14. The system of claim 10, wherein each of the individually removable and replaceable test head umbilicals has a power line, a signal line, and an air line wrapped with a polymer tape.

15. The system of claim 10, wherein the power source is a 24 volt DC continuous supply power source.

16. The system of claim 10, further comprising a tripod for supporting the continuous-real time monitor and display device.

17. The system of claim 10, wherein the plurality of pressure indicators includes from two to six pressure indicators, and wherein the plurality of individual air regulators includes from two air regulators to six air regulators.

18. The system of claim 10, wherein the multiport manifold comprises from twelve compressed air conduits to sixty compressed air conduits.

* * * * *